United States Patent
Ghidoni et al.

(10) Patent No.: US 9,114,119 B2
(45) Date of Patent: Aug. 25, 2015

(54) USE OF SERINE PALMITOYL TRANSFERASE INHIBITORS FOR PREVENTING AND DELAYING INHERITED RETINAL DEGENERATIONS AND COMPOSITIONS THEREOF

(75) Inventors: Riccardo Ghidoni, Milan (IT); Enrica Strettoi, Pisa (IT); Maria Claudia Gargini, Pisa (IT); Paolo Gasco, Turin (IT)

(73) Assignees: Universita' degli Studi di Milano, Milan (IT); Consiglio Nazionale delle Ricerche, Rome (IT); Universita' degli Studi de Pisa, Pisa (IT); Nanovactor S.R.L., Turin (IT)

( * ) Notice: Subject to any disclaimer, the term of this patent is extended or adjusted under 35 U.S.C. 154(b) by 74 days.

(21) Appl. No.: 13/203,340

(22) PCT Filed: Feb. 23, 2010

(86) PCT No.: PCT/EP2010/001119
§ 371 (c)(1),
(2), (4) Date: Oct. 28, 2011

(87) PCT Pub. No.: WO2010/097201
PCT Pub. Date: Sep. 2, 2010

(65) Prior Publication Data
US 2012/0040007 A1    Feb. 16, 2012

(30) Foreign Application Priority Data
Feb. 26, 2009    (IT) .............................. MI2009A0284

(51) Int. Cl.
*A61K 9/14* (2006.01)
*A61P 27/02* (2006.01)
*A61K 31/201* (2006.01)
*B82Y 5/00* (2011.01)
*A61K 31/00* (2006.01)

(52) U.S. Cl.
CPC ............... *A61K 31/201* (2013.01); *A61K 31/00* (2013.01)

(58) Field of Classification Search
None
See application file for complete search history.

(56) References Cited

U.S. PATENT DOCUMENTS

| 2007/0071756 | A1* | 3/2007 | Peyman ..................... 424/155.1 |
| 2008/0027088 | A1* | 1/2008 | Homan et al. ................ 514/275 |
| 2008/0249274 | A1 | 10/2008 | Blackmon et al. |
| 2008/0287479 | A1* | 11/2008 | Hutchings et al. ............ 514/278 |

FOREIGN PATENT DOCUMENTS

| CN | 1 857 218 A | | 11/2006 |
| EP | 0 526 666 A1 | | 2/1993 |
| WO | 2004/039351 A2 | | 5/2004 |
| WO | WO-2004-039351 | * | 5/2004 |
| WO | WO-2004039351 | * | 5/2004 |

(Continued)

OTHER PUBLICATIONS

Hamel, Retinitis pigmentosa, Orphanet Journal of Rare Disease, I:40, Oct. 2006, p. 8.*

(Continued)

*Primary Examiner* — Ernst V Arnold
*Assistant Examiner* — Jianfeng Song
(74) *Attorney, Agent, or Firm* — Silvia Salvadori, P.C.

(57) ABSTRACT

The method for preventing and delaying inherited retinal degenerations using serine palmitoyltransferase inhibitors, and compositions which contain them.

7 Claims, 1 Drawing Sheet

(56) References Cited

FOREIGN PATENT DOCUMENTS

| WO | 2005/092325 | A1 | 10/2005 | |
| WO | 2008/046071 | A2 | 4/2008 | |
| WO | 2008/083280 | A1 | 7/2008 | |
| WO | 2008/084300 | A | 7/2008 | |
| WO | WO-2008-084300 | * | 7/2008 | |
| WO | WO 2008084300 | * | 7/2008 | ........... C07D 401/04 |

OTHER PUBLICATIONS

Acharya et al., Modulating Sphingolipid Biosynthetic Pathway Rescues Photoreceptor Degeneration, Science, vol. 299, Mar. 2003, 1740-1743.*

Acharya et al., "Modulating Sphingolipid Biosynthetic Pathway Rescues Photoreceptor Degeneration", Science, vol. 299, Mar. 2003, 1740-1743.*

Fox et al. "The clinical potential of sphingolipid-based therapeutics", Cell. Mol. Life Sci., Mar. 2006, 1017-1023.*

Wernet et. al, "Building a retinal mosaic: Cell-fate decision in the fly eye", TRENDS in Cell biology, 576-584, vol. 14 No. 10, Oct. 2004.*

Acharya et al.: "Modulating sphingolipid biosynthetic pathway rescues photoreceptor degeneration.", Science (Washington D.C.), vol. 299, No. 5613, Mar. 14, 2003. pp. 1740-1743, XP00255008, ISSN: 0036-8075, abstract, p. 1740, middle column, paragraph 1-p. 1741, left-hand column, paragraph 1, p. 1742, left-hand column, paragraph 2-middle column, paragraph 1.

Database WPI Week 200733, Thomson Scientific, London, GB; AN 2007-344606, XP002550009.

International Search Report, dated Jun. 18, 2010, from corresponding PCT application.

* cited by examiner

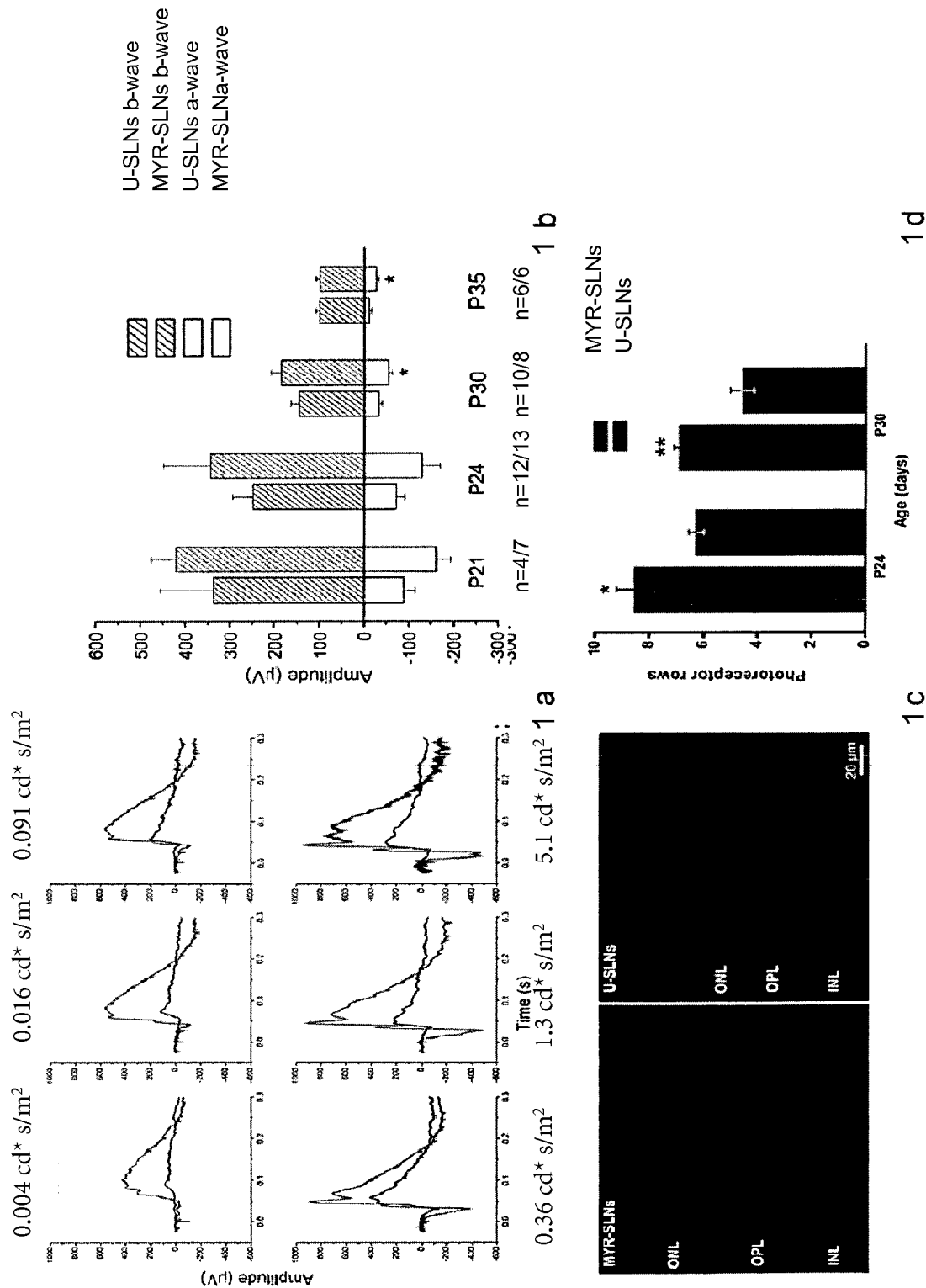

USE OF SERINE PALMITOYL TRANSFERASE INHIBITORS FOR PREVENTING AND DELAYING INHERITED RETINAL DEGENERATIONS AND COMPOSITIONS THEREOF

TECHNICAL FIELD OF THE INVENTION

The present invention relates to the use of serine palmitoyltransferase inhibitors for preventing and delaying inherited retinal degenerations, and to compositions, in particular based on lipid nanospheres, which contain them.

STATE OF THE ART

The term retinitis pigmentosa (RP) comprises a group of inherited disorders which involve progressive degeneration of the retinas of both eyes. The affected individuals suffer a gradual loss of night vision and a reduction of the peripheral visual field (known as "tunnel vision"), and with time central vision may also be lost and the disease can progress up to hypovision and blindness. Another typical characteristic is the increased sensitivity to glare, in other words the delayed adaptation in the change from light to darkness and vice versa. The disorder may affect the photoreceptors (the cones and predominantly the rods, responsible for peripheral vision) or the retinal pigment epithelium, with a characteristic deposit of pigment, to which the name of the disease is due.

Retinitis pigmentosa affects approximately one person in 4000, is found all over the world and is currently untreatable. At least 15,000 persons in Italy are affected, hyposighted, without effective treatment, with an evident economic and social impact. At least 150,000 individuals in the EU suffer from this incurable disorder. As the disease is inherited but does not affect the reproductive capacity, its incidence is tending to increase due to the increased life expectancy in the industrialised countries.

Hodge W G, et al (Can J Ophthalmol. 2006 August; 41(4): 481-90) describe the potential use of omega-3 fatty acids to treat disorders of the retina and of the lens, and in particular to prevent or delay the progression of retinitis pigmentosa. However, the authors emphasise that clinical trials are at the preliminary stage.

The use of some neurotrophic factors has been proposed, however it is still at the experimental stage and is limited by the fact that these substances have a protein structure, a high molecular weight and do not freely permeate the cells. In particular, Thanos C., Emerich D. (Expert Opin Biol Ther. 2005 November; 5(11):1443-52) describe the controlled release of neurotrophic factors such as CNTF, BDNF, GDNF, LEDGF, PEDF and others for the treatment of retinal disorders such as retinitis pigmentosa, macular degeneration, glaucoma and the like.

According to some authors, oral treatment with antioxidants, such as docosahexaenoic acid (DHA), or with diet supplements, such as vitamin A palmitate, delays secondary degeneration of the retinal cones. However, the efficacy of these treatments is still controversial among the scientific community. Berson E L. (Int Ophthalmol Clin. 2000 Fall; 40(4):93-111) describes an attempt to treat degenerative retinal disorders affecting the photoreceptors with nutritional approaches, such as Vitamin A, E, K and B6 supplements, low-protein diets, and the like.

Hyperbaric treatment is not particularly effective, although some studies have observed a positive cell response, demonstrated instrumentally with an electroretinogram (ERG), which showed a statistically significant increase in amplitude in patients treated with oxygen in a hyperbaric chamber.

SUMMARY OF THE INVENTION

It has now been found that the administration in vivo of non-toxic quantities of inhibitors of serine palmitoyltransferase, the enzyme that catalyses the first critical stage of ceramide biosynthesis, is able to delay the progress of the disorder, i.e. of retinitis pigmentosa, by reducing the degeneration rate of the photoreceptors, prolonging their survival and improving their functional performances, and especially the time window of residual vision.

It has also been found that the use of a lipid nanosphere formulation not only allows the nanospheres to be loaded with the serine palmitoyltransferase inhibitor obtaining aqueous dispersions with concentrations comparable to those used for intraocular injections, but also provides a high concentration of the compound on the retina, especially at the interface with the retinal pigment epithelium, releasing the drug and not causing toxicity.

BRIEF DESCRIPTION OF THE DRAWINGS

FIG. 1a shows histological sections of retinas.

FIG. 1b shows a quantitative analysis of the average number of rows of nuclei in ONL (outer nuclear layer) of MYR-SLN (Myriocin-Solid Lipid Nanospheres) and U-SLN (Unloaded-Solid Lipid Nanospheres) treated mice.

FIG. 1c shows retinal vertical sections from two SLN treated mice.

FIG. 1d shows T-test analysis of photoreceptor nuclear rows.

DESCRIPTION OF THE INVENTION

The present invention relates to the use of serine palmitoyltransferase (SPT) inhibitors for preventing and delaying inherited retinal degenerations, i.e. retinitis pigmentosa, and to compositions based on lipid nanospheres which contain SPT inhibitors.

Examples of serine palmitoyltransferase inhibitors include myriocin and the compounds specified in the following bibliographical references.

Sasaki, S. et al., J. Antibiot. 47: 420-33 (1994) describe mycestericins, compounds structurally correlated with myriocin, as SPT inhibitors.

VanMiddlesworth F., et al., J. Antibiotics 45: 861-7 (1992) describe another class of potent SPT inhibitors, the sphingofungins.

Other SPT inhibitors include cycloserine, D-serine, viridiofungin A and lipoxamycin.

US 20080249274 describes methods for the treatment of atherosclerosis through administration of myriocin.

WO 2005092325 describes the use of myriocin for the preparation of a medicament for the treatment of hypertriglyceridaemia in mammals.

WO 2008046071 describes compounds with SPT-modulating activity for the treatment of insulin resistance, cardiovascular disorders, metabolic syndrome and inflammatory disorders.

WO 2008083280 describes compounds which act on SPT, useful for treating insulin resistance, pancreatic beta-cells apoptosis, obesity, cardiovascular disorders, dyslipidaemias and fragile X syndrome.

WO 2004039351 describes pharmaceutical compositions containing lipid nanoparticles which are suitable for use in ophthalmic field.

More particularly, the present invention relates to the use of myriocin for preventing and delaying inherited retinal degenerations, i.e. retinitis pigmentosa, and compositions based on lipid nanospheres loaded with myriocin.

Myriocin is a natural compound, of fungal origin, soluble in the membranes and able to penetrate the cells freely, with an inhibiting action on serine palmitoyltransferase.

The administration of myriocin induces inhibition of de novo synthesis of ceramide, a sphingolipid present in murine RP models.

It has been found that myriocin, administered in the retina, is able to act directly on the metabolic pathways of the photoreceptors, selectively inhibiting a metabolic pathway which is activated during photoreceptor cell death in the inherited retinal degenerative disorder, and thus partly inhibiting the death of the photoreceptors affected by RP.

However, it should be noted that myriocin has no effect, also unfavourable, on normal cells. This compound may therefore be used to delay the progressive degeneration process of the photosensitive retinal cells in retinitis pigmentosa, thus prolonging the phase of usable vision in the subject affected by that disorder. Since this is a slowly progressing disorder, a delay, even a partial delay, involves a considerable improvement in the visual performance of the affected subject, and therefore improves his/her quality of life.

It has been found that the administration of myriocin in vivo to experimental animals induces selective changes among the photoreceptors of the retina, whose survival is prolonged, and a concomitant decrease in the degeneration rate of these cells is observed.

Moreover, an increased visual performance of the retina, measured with electroretinographic methods, has been observed.

Myriocin treatment inhibits the active process of retinal cell death, regardless of the mutation causing it. This is an enormous advantage of the method used, since the major difficulties involved in treating RP are due to its great genetic heterogeneity.

Experimental Section

Studies designed to investigate the efficacy of myriocin in the treatment of RP were conducted on an rd10 mutant mouse model. This mouse presents a missense mutation of the beta sub-unit of the rod-specific phosphodiesterase gene, and mimics a form of autosomal recessive human RP. Rod death begins at around 12 days of life (P12), and peaks at P24, as demonstrated by the fact that an ERG (electroretinogram) generated by the rods can be recorded up to P25. As regards the death of retinal cones, the responses are extinguished at P45.

Rod degeneration presents the characteristic features of apoptosis.

A multidisciplinary approach, based on biochemistry, morphology and electrophysiology, was used to establish photoreceptor death as the objective through sphingolipid signalling in the rd10 mutant mouse, and the following results were obtained:

A. Endogenous Ceramide Levels

The levels of the sphingolipid endogenous ceramide were tested after isolation of the retina from anaesthetised rd10 mutant and wild-type (wt) mice of various age groups. The isolated retinas were treated for lipid extraction, and the total endogenous ceramide/inorganic phosphate ratio was determined with the diacylglycerol kinase test. It was found that the endogenous ceramide levels increase in the retina of rd10 mutant mice at the time of massive photoreceptor degeneration, and remain constantly elevated at all the ages tested. Conversely, the retinal ceramide levels in the wild-type (wt) control animals with the same genetic background did not change after full retinal maturity.

These results indicate that ceramide plays a causative role in the apoptotic process which affects the photoreceptors, leading to their death. So the residual retinal cells, which are known to degenerate progressively (e.g. the cones, and the bipolar and horizontal rod cells) may therefore die as a result of a ceramide-dependent process.

B. Reduction in Endogenous Ceramide Levels Following Myriocin Treatment

Single intravitreal injections of 500 nanoliters of myriocin (188 mM) were administered to the right eye of rd10 and wt mice aged P19. The vehicle alone (DMSO) was injected into the left eye of the same animals. The left and right retinas were isolated at P21, and treated separately for the biochemical ceramide test as explained above.

Significantly lower ceramide levels were consequently found in the eyes of the rd10 mice treated with myriocin than in the control eyes. This reduction in ceramide levels corresponded to a marked reduction in the number of pyknotic (dying) photoreceptors in the rd10 mutant mice, as demonstrated by the following quantitative morphological method.

Conversely, the myriocin injection did not significantly reduce the retinal ceramide levels in the wt mice.

C. Pyknotic Photoreceptor Count

The animals injected at P19 were collected at P21, and their eyes were enucleated and fixed. The left and right retinas were isolated, stained with fluorescent DNA-binding molecules, and mounted on slides. The external nuclear layer which contains the photoreceptor cores was sampled under the confocal microscope at regular intervals along the four retinal meridians. The images were exported to a computerised workstation, and the pyknotic photoreceptors were counted in each scanned field. The total number of pyknotic photoreceptors was calculated for each pair of treated and control retinas.

It was found that the myriocin injection reduces the photoreceptor death rate by approx. 50% (n=17 rd10 mice used, 34 eyes injected and counted). The estimated number of pyknotic photoreceptors in the retinas treated only with DMSO remained in the same range previously observed for the retinas of the untreated rd10 mice used for other studies.

D. Histological Observations

From the histological standpoint, it was observed that the rd10 and wt mice injected with myriocin presented normal retinal morphologies. Moreover, the retinas of the mice with GFP (Green Fluorescent Protein) in ganglion cells (Thy1-GFP mice), injected like the others, showed excellent maintenance of the morphology of the ganglion cell and structure, and the retinal stratification was good on the whole.

E. Toxicity Studies

Control experiments conducted before and during the studies illustrated above demonstrated that intraocular injections of myriocin do not cause adverse effects on either rd10 or wt mice. It should be noted that myriocin has only rarely been used in vivo to date, and never injected intraocularly. The dose was chosen on the basis of the available literature on cultured cells, calculating a dilution of 7/8 times, due to the vitreous humour. A time window was selected for intraocular administration which preceded the peak death of the apoptotic photoreceptors, for the crucial reason of preventing the majority of photoreceptors from entering the apoptotic cycle. Finally, toxic effects were excluded on the basis of the fact that no general or local inflammatory response symptoms (e.g. invasion by macrophages) or increased ocular reactivity were ever observed in the treated animals.

F. Functional Recovery of Photoreceptors

The functional recovery of the photoreceptors was studied by recording a flash electroretinogram (ERG), a technique widely used to test the retinal physiology of human patients, especially those suffering from RP.

Two groups of rd10 mice injected intraocularly as described above presented no recovery of ERG response/reaction in the eye injected with myriocin compared with the other eye injected with the vehicle, suggesting that the dose of myriocin administered with a single injection was too low to produce detectable changes in a marked reaction of the photoreceptors to light. Even repeated intravitreal injections of myriocin did not constitute a protocol suited to the small size of the eyes of the mice (and the same mice at approx. P19): repeated general anaesthetics and intraocular injections involve a high risk of death of the animals and development of cataracts respectively.

A new, non-invasive method of myriocin administration was therefore developed, based on the use of lipid nanospheres. These are particles consisting of lipids with a mean diameter preferably of between 40 and 240 nanometers, produced according to EP 526666 and WO 2004039351. As a result of the use of that formulation it was possible to load lipid nanospheres with myriocin, obtaining an aqueous dispersion at a concentration comparable with that used for intraocular injections.

The ability of fluorescent nanospheres, loaded of fluorescent dye and not loaded with the active ingredient (empty), to reach the interior of the eye was first evaluated. On observation with the confocal microscope it was found that 24 hours after the administration of these nanospheres to the eye surface, the fluorescent particles were highly concentrated on the retina, especially on the interface with the pigment epithelium.

Lipid nanospheres loaded with myriocin at a concentration of 0.27 mg/mL were administered to litters of rd10 mutant mice. When their eyes opened (P14), each litter was divided into two groups: the first group received nanospheres loaded with myriocin in the form of eyedrops every day (750 nanoliters per eye), and the second received unloaded (empty) nanospheres, with the same chemical formulation but without myriocin. The ERG recordings taken to evaluate possible functional recovery of the photoreceptors began at P21 (the age when recordable ERGs are greatest in this mutant), and continued to P30. In the untreated rd10 animals, the ERGs induced by the rods were extinguished at that age. In the rd10 animals treated with myriocin-loaded nanospheres, the therapeutic effect of the medicament was observed particularly at P24 (peak death of the photoreceptors) and in the interval P28-P30. At this late age, a clear cone-induced response persisted in the animals treated with myriocin, compared to the control group.

The persistence of cone-induced responses after the time of total extinction of ERG in the rd10 mutant mice is a very important result. The residual vision of human RP patients is based on the cones, which are inexorably destined to die after the death of the rods.

Following ERG recordings, animals were enucleated, their eyes fixed and sectioned and retinal sections stained with fluorescent nuclear dyes to evaluate the thickness of the outer nuclear layer (ONL) and the overall retinal morphology.

Histological sections of the same retinas from which the ERGs were obtained are shown in FIG. 1a.

ERG responses to flashes of light of increasing intensities were obtained from two rd10 mice aged P24. Larger grey traces are responses from one MYR-SLN (Myriocin-Solid Lipid Nanospheres) treated mouse while black traces are from a control animal.

The number of preserved nuclear rows in the ONL is significantly higher in the myriocin-treated than in the control mouse.

A quantitative analysis of the average number of rows of nuclei in the ONL of MYR-SLN and U-SLN (Unloaded-Solid Lipid Nanospheres) treated mice is given in FIG. 1b.

Plots of scotopic ERG responses obtained from a cohort of rd10 mice aged P21-P35 are shown. Positive values indicate the b-wave and negative values indicate the a-wave amplitudes of the ERG. Mice treated with MYR-SLN (grey diagrams) show better a-wave responses in the time window P27-P35 (*:$p<0.05$ Wilcoxson-Mann-Whitney test).

FIG. 1c shows retinal vertical sections from the two SLN treated mice from which ERG traces on the left were recorded. The number of photoreceptor rows in the MYR-SLN treated animals is higher than in the control, indicating increased survival.

In FIG. 1d T-test analysis shows that the number of photoreceptor nuclear rows is higher in MYR-SLN treated retinas in the P24-P30 time interval.

Consequently, continual administration of myriocin in the form of lipid nanospheres constitutes a non-invasive way of protecting the photoreceptors from progressive degeneration in retinitis pigmentosa.

G. Discussion

The results described above demonstrate that it is possible to reduce the apoptotic death rate of photoreceptors by reducing the retinal ceramide levels through inhibition of de novo ceramide biosynthesis.

The results obtained therefore demonstrate that a reduction in photoreceptor degeneration can be maintained after administration of myriocin. Consequently, the use of myriocin according to the invention can be considered an effective therapeutic strategy to help keep the photoreceptors (which are otherwise destined to die) viable for a longer period of time.

This is particularly interesting in view of the fact that the moderately aggressive phenotype and maintenance of the retinal architecture typical of the rd10 mutant mouse identify patients with recessive phosphodiesterase mutations as possible candidates for gene treatment.

It is also generally believed that a small increase in the rod survival rate would probably lead to proportionally longer viability of the cones.

For the recommended therapeutic uses, the compositions according to the invention may preferably be formulated, as described above, in the form of lipid nanospheres for topical ocular administration, which constitute one aspect of the present invention. The method of preparing said nanospheres, as indicated above, is disclosed in EP 526666 and WO 2004039351.

The compositions according to the invention can also be formulated in other ways suitable for topical ocular administration, for example in the form of eyedrops or injections for ophthalmic use, such as intravitreal, subconjunctival, intracameral or retrobulbar injections, possibly using suitable excipients, where permitted, and may be prepared according to conventional methods well known in pharmaceutical technology, such as those described in "Remington's Pharmaceutical Handbook", Mack Publishing Co., N.Y., USA.

The invention claimed is:

1. A method for treating and delaying retinitis pigmentosa, comprising administering an effective amount of myriocin to a subject in need thereof.

2. The method of claim 1, wherein the myriocin is administered in pharmaceutical form suitable for ophthalmic administration.

3. The method of claim 2, wherein said pharmaceutical form is in the form of lipid nanospheres.

4. A method of reducing the degeneration of photoreceptor cells in a subject having retinitis pigmentosa, comprising ocularly administering an effective amount of myriocin to a subject in need thereof.

5. A method of inhibiting de novo synthesis of ceramide in a subject having retinitis pigmentosa, comprising administering an effective amount of myriocin to a subject in need thereof.

6. The method of claim 1, wherein the myriocin is administered to the subject ocularly.

7. The method of claim 6, wherein the myriocin is administered to the subject by intravitreal, subconjunctival, intracameral or retrobular injection.

\* \* \* \* \*

UNITED STATES PATENT AND TRADEMARK OFFICE
CERTIFICATE OF CORRECTION

PATENT NO. : 9,114,119 B2  
APPLICATION NO. : 13/203340  
DATED : August 25, 2015  
INVENTOR(S) : Ghidoni et al.

Page 1 of 1

It is certified that error appears in the above-identified patent and that said Letters Patent is hereby corrected as shown below:

Title Page

Column 1, item (73) Assignees:

Nanovactor S.R.L., Turin (IT) should read "Nanovector S.R.L., Turin, (IT)"

Signed and Sealed this
Twenty-second Day of December, 2015

Michelle K. Lee
*Director of the United States Patent and Trademark Office*